United States Patent [19]

Kees et al.

[11] Patent Number: 4,728,739
[45] Date of Patent: Mar. 1, 1988

[54] HYPOGLYCEMIC THIAZOLIDINEDIONES

[75] Inventors: Kenneth L. Kees, West Chester; Robert S. Cheeseman, Swedeland, both of Pa.

[73] Assignee: American Home Products Corporation, New York, N.Y.

[21] Appl. No.: 62,268

[22] Filed: Jun. 15, 1987

[51] Int. Cl.[4] .......................... C07D 277/34
[52] U.S. Cl. .................................. 548/183
[58] Field of Search ........................ 548/183

[56] References Cited

U.S. PATENT DOCUMENTS

4,461,902  7/1984  Kawamatsu .................. 548/183

FOREIGN PATENT DOCUMENTS

84926  1/1983  European Pat. Off. ............ 548/183

OTHER PUBLICATIONS

Fujita et al., Diabetes 32, 804 (1983).
Sohda et al., Chem. Pharm. Bull., 32(6), 2267-2278 (1984).
Derwent Abstract, 84-104874/17 of J5 9048471.
Derwent Abstract 15148C/09 of EP 9203.
Stout, Metabolism, 34(12), 7-12, Supp. 1 (1985).

*Primary Examiner*—Robert Gerstl
*Attorney, Agent, or Firm*—Richard K. Jackson

[57] ABSTRACT

The compounds:

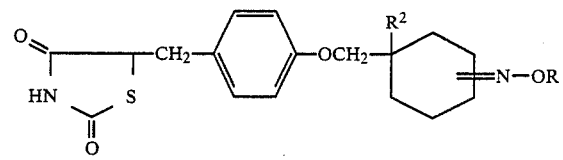

in which R is hydrogen, lower alkyl, phenyl or benzyl, and $R^2$ is hydrogen or lower alkyl, or a pharmaceutically acceptable salt thereof, are useful hypoglycemic and hypoinsulinemic agents for the treatment of diabetes mellitus and cardiovascular disease states involved in elevated insulin levels such as atherosclerosis.

4 Claims, No Drawings

HYPOGLYCEMIC THIAZOLIDINEDIONES

BACKGROUND OF THE INVENTION

Ciglitazone (5-[4-(1-methylcyclohexylmethoxy)benzyl]thiazolidine-2,4-dione) has been established as effective in the treatment of hyperglycemia and hyperinsulinemia [Fujita et al., Diabetes 32, 804 (1983)]. The metabolites of ciglitazone have been identified and their pharmacological properties studied [Sohda et al., Chem. Pharm. Bull. 32 (6) 2267–2278 (1984); Derwent Abstract 83-730351/32 of EP 84926]. Various derivatives of the ciglitazone have been studied, including alkylsubstitution of the cyclohexyl moiety [Derwent Abstract 84-104874/17 of J5 9048471] and alkoxy modifications of the moiety para- on the benzyl group (Derwent Abstract 15148C/09 of EP 8203).

DESCRIPTION OF THE INVENTION

In accordance with this invention, there is provided a group of substituted thiazolidine analogues of the formula:

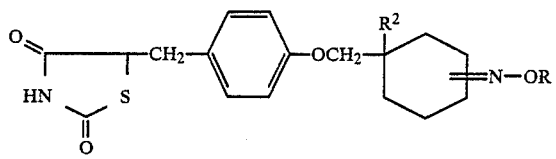

in which

R is hydrogen, alkyl of 1 to 6 carbon atoms, phenyl or benzyl; and $R^2$ is hydrogen or alkyl of 1 to 4 carbon atoms;

or a pharmaceutically acceptable salt thereof.

The preferred oximes of this invention are those of the above structural formula where R is hydrogen or alkyl of 1 to 3 carbon atoms and $R^2$ is hydrogen or methyl, most preferably methyl.

The pharmaceutically acceptable salts are produced conventionally by neutralization with an inorganic or organic base such as an alkali metal hydroxide, ammonium hydroxide, a mono- or di(lower)alkylamine, and the like.

The compounds of this invention are prepared by conventional methods involving the base catalyzed reaction of hydroxylamine or an alkoxylamine with the appropriately substituted ketone, thusly:

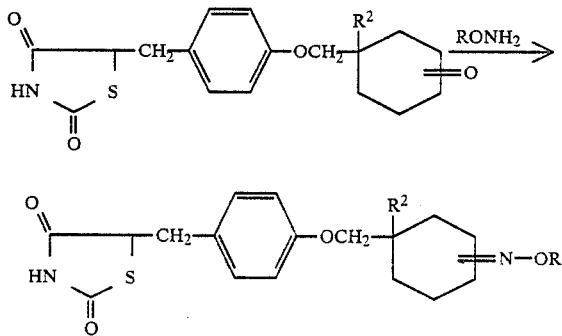

The following examples illustrate the production of representative compounds of this invention.

EXAMPLE 1

5-[[4-[(1-methyl-2-hydroxyiminocyclohexyl)methoxy]-phenyl]methyl]-2,4-thiazolidinedione A mixture of 5-[[4-[(1-methyl-2-oxocyclohexyl)methoxy]phenyl]methyl]-2,4-thiazolidinedione (3 g), sodium acetate (0.78 g) and hydroxylamine hydrochloride (0.66 g) were suspended in ethanol (50 mL) and refluxed overnight. The reaction mixture was cooled to room temperature, filtered, and the filtrate concentrated on the rotary evaporator. The residue was dissolved in ethyl acetate (300 mL) and washed with water (200 mL) and saturated sodium chloride solution (200 mL). After further drying with anhydrous $MgSO_4$, the product was filtered and concentrated to give 2.73 g (87% yield) of oxime, as a pale yellow solid, m.p. 55°–59° C.

Elemental Analysis for: $C_{18}H_{22}N_2O_4S$

Calculated: C, 59.65; H, 6.12; N, 7.73. Found: C, 59.29; H, 6.21; N, 7.36.

EXAMPLE 2

5-[[4-[(1-methyl-2-methoxyiminocyclohexyl)methoxy]-phenyl]methyl]-2,4-thiazolidinedione A mixture of 5-[[4-[(1-methyl-2-oxocyclohexyl)methoxy]phenyl]methyl]-2,4-thiazolidinedione (3 g), sodium acetate (0.78 g) and O-methylhydroxylamine hydrochloride (0.66 g) were suspended in ethanol (200 mL) and refluxed overnight. The reaction mixture was concentrated in vacuo and the residue dissolved in ethyl acetate and dried over $MgSO_4$. Filtration and concentration left 3.25 g of yellow oil which was purified by high pressure liquid chromatography. The product, 2.21 g of yellow oil, was dissolved in ethanol (100 mL) and stirred overnight at room temperature with KOH (0.35 g). The solvent was removed using a rotary evaporator, ethyl acetate was added, and the product was dried over $Na_2SO_4$. After filtration and concentration, the product was dried overnight under vacuum at room temperature to give 1.79 g of thepotassium salt of the title compound as a white solid, which fuses at 135°–138° C.

Elemental Analysis for: $C_{19}H_{24}N_2O_5SK \cdot \frac{1}{2}H_2O$

Calculated: C, 53.87; H, 5.71; N, 6.61. Found: C, 54.12; H, 5.52; N, 6.36.

The compounds of this invention are useful hypoglycemic and hypoinsulinemic agents. As such they are useful in the treatment of diabetes mellitus and associated cardiovascular disease problems currently related to elevated insulin levels, such as atherosclerosis [Stout, Metabolism, 34 (12), 7–12, Supp. 1 (1985)]. Their ability to act in that capacity was established by their activity profile when tested in standard experimental animals in accordance with the following procedure:

Eight to ten week old genetically obese (ob/ob) mice are randomly placed in groups of nine animals. The compound being tested is administered in single doses orally for four consecutive days. A blood sample is taken on the fifth day at the normal dosing time. The concentration of insulin and glucose in plasma obtained from the blood samples is determined and reported as the mean ± standard error for each test group of nine animals and compared to vehicle control and ciglitazone as the standard.

The data obtained from several experiments comparing the products of Examples 1 and 2 with ciglitazone and the vehicle control is presented in the following table. Special attention is drawn to the results obtained with the preferred compound, the product of Example 1, as demonstrating effective glucose lowering and superior insulin lowering activity as representing an especially desirable selective activity profile for treatment of cardiovascular disease states such as atherosclerosis.

TABLE

| Experiment | Drug | Dose (mg/kg) | Glucose (mg/dl) | Insulin (μml) |
|---|---|---|---|---|
| 1 | control | — | 154 ± 10 | 182 + 9 |
|   | Ciglitazone | 75 | 89 ± 7* | 57 ± 7* |
|   | Example 1 | 75 | 94 ± 3* | 45 ± 2* |
| 2 | control | — | 139 ± 8 | 167 ± 14 |
|   | Ciglitazone | 5 | 127 ± 5 | 156 ± 12 |
|   | Example 1 | 5 | 105 ± 6* | 63 ± 7* |
| 3 | control | — | 137 ± 7 | 168 ± 24 |
|   | Ciglitazone | 5 | 101 ± 7* | 170 ± 10 |
|   |   | 20 | 97 ± 7* | 116 ± 14* |
|   |   | 75 | 92 ± 4* | 59 ± 8* |
|   | Example 1 | 2 | 131 ± 7 | 168 ± 17 |
|   |   | 5 | 106 ± 6* | 112 ± 14* |
|   |   | 20 | 91 ± 3* | 51 ± 5* |
|   |   | 75 | 87 ± 3* | 31 ± 7* |
| 4 | control | — | 120 ± 7 | 229 ± 25 |
|   | Ciglitazone | 20 | 76 ± 5* | 183 ± 20 |
|   | Example 2 | 20 | 81 ± 7* | 137 ± 16* |

*Significantly different from control values by unpaired test, $p < 0.05$.

From the experimental data obtained, it is apparent that the compounds of this invention are potent anti-hyperglycemic and anti-hyperinsulinemic agents useful in the treatment of disease states characterized by abnormally high blood levels of glucose and/or insulin, such as diabets mellitus and cardiovascular diseases, such as atherosclerosis. As such, the compounds of this invention are to be administered to a mammal suffering from excessive blood levels of glucose and/or insulin in an amount from about 5 mg/kg to about 300 mg/kg body weight or more per day. An optimum dosing regimen to achieve the desired therapeutic response must be individualized for the patient by following the post-administration glucose and/or insulin blood levels. The dosage will vary with the compound administered and with the patient's age, weight, severity of disease state, response, etc., as is common in all therapeutic-methods for control of glucose and insulin levels. One advantage evidenced by the experimental testing of the compounds of this invention is that they tend only to normalized blood glucose levels, thereby avoiding any problem of precipitating hypoglycemic shock.

The compounds of this invention are orally active and may be made up in conventional unit dosage forms for administration. Compositions with inert diluents or edible carriers are compressed into tablets or filled in hard or soft gelatin capsules, with sufficient active ingredients to supply a daily dose or any fraction thereof. Slow release formulations are especially suitable for control of glucose and insulin with the compounds of this invention.

What is claimed is:

1. A compound of the formula:

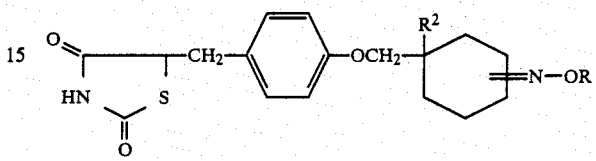

in which
R is hydrogen, alkyl of 1 to 6 carbon atoms, phenyl or benzyl; and
$R^2$ is hydrogen or alkyl of 1 to 4 carbon atoms;
or a pharmaceutically acceptable salt thereof.

2. A compound of claim 1 of the formula:

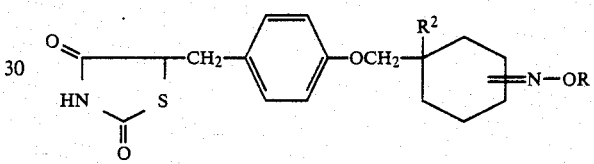

in which
R is hydrogen or alkyl of 1 to 3 carbon atoms; and
$R^2$ is hydrogen or methyl;
or a pharmaceutically acceptable salt thereof.

3. The compound of claim 1 which is 5-[[4-[(1-methyl-2-hydroxyiminocyclohexyl)methoxy]phenyl]methyl]-2,4-thiazolidinedione, or a pharmaceutically acceptable salt thereof.

4. The compound of claim 1 which is 5-[[4-[(1-methyl-2-methoxyiminocyclohexyl)methoxy]phenyl]methyl]-2,4-thiazolidinedione, or a pharmaceutically acceptable salt thereof.

* * * * *